US008734321B1

(12) United States Patent
Weller

(10) Patent No.: US 8,734,321 B1

(45) Date of Patent: May 27, 2014

(54) SYSTEMS AND METHODS FOR PROVIDING SEXUAL STIMULATION

(76) Inventor: Eric P. Weller, Lynnwood, WA (US)

(*) Notice: Subject to any disclaimer, the term of this patent is extended or adjusted under 35 U.S.C. 154(b) by 624 days.

(21) Appl. No.: 13/070,562

(22) Filed: Mar. 24, 2011

Related U.S. Application Data

(60) Provisional application No. 61/317,066, filed on Mar. 24, 2010.

(51) Int. Cl.
*A61F 5/00* (2006.01)

(52) U.S. Cl.
USPC .......... 600/38

(58) Field of Classification Search
CPC ....... A61H 7/001; A61H 7/002; A61H 7/004; A61H 39/04; A61H 2201/5007; A61H 2201/1669; E21B 3/02; E21B 44/04
USPC ........ 600/38–41; 601/66, 110, 115, 116, 107, 601/108, 111
See application file for complete search history.

(56) References Cited

U.S. PATENT DOCUMENTS 3,504,665 A * 4/1970 Bakunin et al. ........ 601/71
4,046,142 A * 9/1977 Whitney ........ 601/108
5,460,597 A * 10/1995 Hopper ........ 601/84
6,272,819 B1 * 8/2001 Wendte et al. ........ 56/11.9
6,632,185 B2 * 10/2003 Chen ........ 601/101
7,571,904 B2 * 8/2009 Bober ........ 270/58.12
8,360,956 B2 * 1/2013 Squicciarini ........ 600/38
2010/0160840 A1 * 6/2010 Murphy ........ 601/112

* cited by examiner

*Primary Examiner* — Samuel Gilbert

(74) *Attorney, Agent, or Firm* — Puget Patent; Michael Gibbons

(57) ABSTRACT

A handheld device for providing sexual stimulation includes a plurality of paddles contained by an attachment which can be mounted on a shaft driven by a motor of the device. Control logic of the device ensures that a rotational speed for the device selected via the device's user interface is maintained even when the device is held against a part of a human body. That is, resistance from holding the device against a body part is accounted for, inasmuch as the device senses the resistance and adjusts the motor to maintain the desired rotational speed through the resistance. Different attachments may have different numbers of paddles, and the paddles may be placed differently on different attachments or may have different shapes, among other variations in the paddles. The device is battery-operated, and a charging connection through the device housing is offered through a septum, providing a water-resistant enclosure.

20 Claims, 13 Drawing Sheets

SYSTEMS AND METHODS FOR PROVIDING SEXUAL STIMULATION

PRIORITY CLAIM

This application claims the benefit of U.S. provisional patent application Ser. No. 61/317,066 filed Mar. 24, 2010 (our ref. WLLR-1-1001). The foregoing application is incorporated by reference in its entirety as if fully set forth herein.

FIELD OF THE INVENTION

This invention relates generally to mechanics, and more specifically, to systems and methods for providing sexual stimulation.

BACKGROUND

Receiving oral sex is a pursuit enjoyed by many. For women, cunnilingus may be an especially enjoyable activity. But for some, several impediments to receiving oral sex with the frequency one might desire may exist. Quite simply, one may not have a partner available to perform the act. Or, a potential partner may be unwilling or not present at the time oral sex is desired.

In other situations, a partner is willing and available, but lacks the skill or technique to perform to the satisfaction of the recipient. Other individuals may become fatigued after prolonged periods of providing oral sex. And others may not have any of these problems, but merely desire the variety of a mechanical device to simulate oral sex.

Additionally, some report greater satisfaction or likelihood of gratification with oral sex when the technique integrates various motions or rates of repetition. Some have a difficult time expressing to a partner what technique would bring them the most pleasure. A mechanical device for simulating cunnilingus has an advantage because one does not need to worry about how to frame a request to a partner to vary the technique in a manner that will be effective and without the potential for upset. One can merely change the operating mode of the device.

A mechanical device can also provide a stronger touch, with greater torque, resistance, or rate of repetition. Further, attachments for a mechanical device can provide a different shape or feel such that the device mimics a human tongue, or feels like something else altogether for variety. For example, for individuals who are survivors of sexual abuse, a non-anthropomorphic attachment may be less threatening. Attachments also facilitate simple cleaning without having to disassemble the device.

Additionally, a mechanical device can have a variety of sizes of motors and gearing. Some mechanical devices for sexual pleasure are quite loud or have high rotational speeds that make the device sound like it is whining, which is a distraction and may prevent the device from being pleasurable. If constructed with carefully-selected components, a mechanical device can combine a low rpm motor with gearings to achieve a higher rotational speed of an attachment, minimizing “mosquito-like” whine of the device. The attachment form also ensures the motor is completely enclosed, muting sound from the motor, especially when combined with a sound-absorbing housing.

A mechanical device for providing simulated cunnilingus or other stimulation has many benefits. Accordingly, this application discloses a method and system for providing sexual stimulation.

SUMMARY

This invention relates generally to mechanics, and more specifically, to systems and methods for providing sexual stimulation. In some embodiments, the invention includes a method including applying a device to a part of the body; setting a desired rotational speed for the device; and holding the device more firmly against the part of the body as desired for more pressure. In other embodiments, the invention includes a method including receiving a desired rotational speed; receiving a current pressure value; adjusting the current rotational speed; and sending a rotational speed. In other embodiments, the invention includes a system for providing sexual stimulation, including a user interface, a pressure sensor, a power source, a charging mechanism, a control unit, and a motor. In other embodiments, the invention includes a system for providing sexual stimulation, including a housing, a user interface, a power supply, a motor, a housed shaft, and an attachment. When the user interface is operated, the motor spins the attachment via the housed shaft, and the device is applied to a part of the body providing sexual stimulation. In some embodiments, the invention may include the attachment pressed against the clitoris providing a simulation of cunnilingus. In certain embodiments, the housing is ergonomically designed to provide a comfortable grip when the device is held by either the person being stimulated or by a partner. In certain embodiments, the housing is constructed of a squeezable rubber to minimize vibration and fatigue from holding the device and may be ornately designed with colors, jewels or other designs for a pleasing visual appearance, or may contain lighting features, either for design effect or to cast illumination. In other embodiments, the housing encompasses a reservoir in which lubricant can be stored and dispensed. In certain further embodiments, the port for the charging mechanism is hidden inside the housing, the housing maintaining an airtight seal when there is no charging mechanism connected, but opening slightly when a charging plug is pushed into the housing. In certain further embodiments, the airtight seal of the rubber of the housing is a septum.

In some embodiments, the user interface has separate power and speed controls, may include controls to dispense lubricant, and/or may include controls to change the motion of the device, including gyration, vibration, protrusion/retraction, displacement, and/or similar motions. In a certain embodiment, the user interface is contained in a separate device, which is joined to this system by a wire or by a wireless connection. In some embodiments, the user interface has lighting features and/or still or moving camera functionality and/or is configured to send and/or receive data via wireless and/or wired communication (e.g., to present images to a remote individual and/or to allow that remote individual to at least partially control various aspects of the device for providing sexual stimulation).

In some embodiments, the attachment includes a base having one or more paddles disposed thereon, wherein the one or more paddles are configured to contact a body part (e.g., a sexual body part) upon revolution of the attachment to simulate cunnilingus. In some embodiments, a plurality of attachments are provided, each having a base with different placements, numbers, lengths, shapes, and/or sizes of paddles disposed thereon. In some embodiments, variations of a number of paddles results in variation of contacts/unit of time (e.g., 4 paddles at 100 rpm results in 400 contacts per minute and 8 paddles at 100 rpm results in 800 contacts per minute). In some embodiments, a rotation of paddles of an attachment may be uniform, alternative, and/or random (e.g., successive paddles being rotated slightly relative to one another). In some embodiments, a paddle may be rounded, flat, or some other uniform and/or non-uniform shape. In some embodiments, a plurality of different removable attachments may be provided each having varying numbers, sizes and/or placements of paddles. In some embodiments, an attachment 412 has a varied texture including ridges, nubs, or other protrusions or cavities and/or has a cavity into which another device, such as a vibrating dildo can be inserted, providing sexual stimulation such as penetration into a human body.

BRIEF DESCRIPTION OF THE DRAWINGS

Embodiments of the present invention are described in detail below with reference to the following drawings.

DETAILED DESCRIPTION

The invention relates generally to mechanics, and more specifically, to systems and methods for providing sexual stimulation. Specific details of certain embodiments of the invention are set forth in the following description and in FIGS. 1-13 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1:
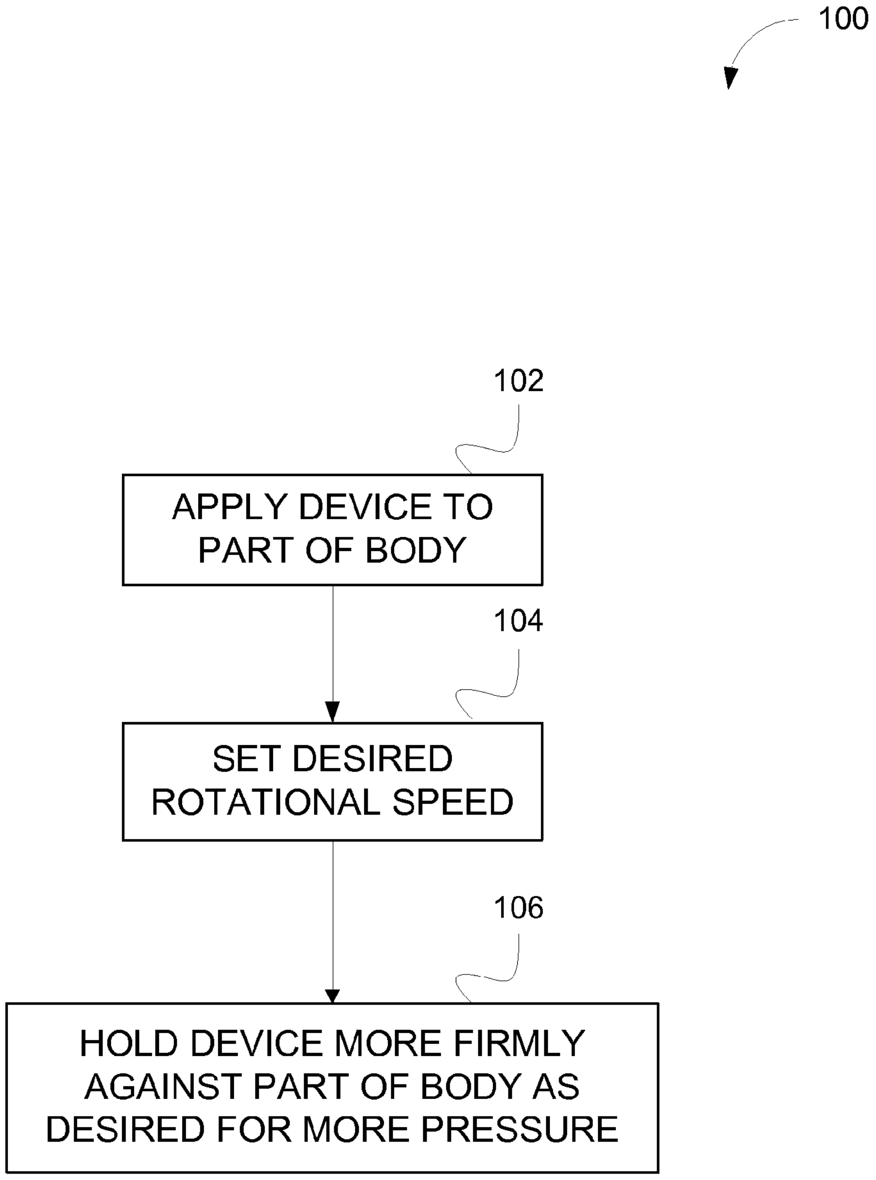
FIG. 1 is a flow diagram of a method for providing sexual stimulation, in accordance with an embodiment of the invention.

FIG. 1 is a flow diagram of a method for providing sexual stimulation, in accordance with an embodiment of the invention. In some embodiments, method 100 is performed using a system for providing sexual stimulation. Method 100 includes applying a device to a part of the body 102; setting a desired rotational speed for the device 104; and holding the device more firmly against the part of the body as desired for more pressure 106. For example, the applying a device to a part of the body 102 may include applying a device to any body part for which stimulation is desired. For example, the device can be applied to the clitoris, the labia, the vulva, or other parts of the anatomy to be stimulated.

The setting a desired rotational speed for the device 104 may include setting any value from a range of rpm. For example, 5 rpm may be a desirable rotational speed for optimal stimulation. During method 100, different rpm can be selected for variety. For example, at the beginning of the stimulation, 5 rpm may be selected, but after a period of time, 10 rpm may be desired and selected.

The holding the device more firmly against the part of the body as desired for more pressure 106 may include barely permitting the device to touch the body part. After a period of time, more pressure may be desired and holding the device more firmly against the body part may be included.

Figure 2:
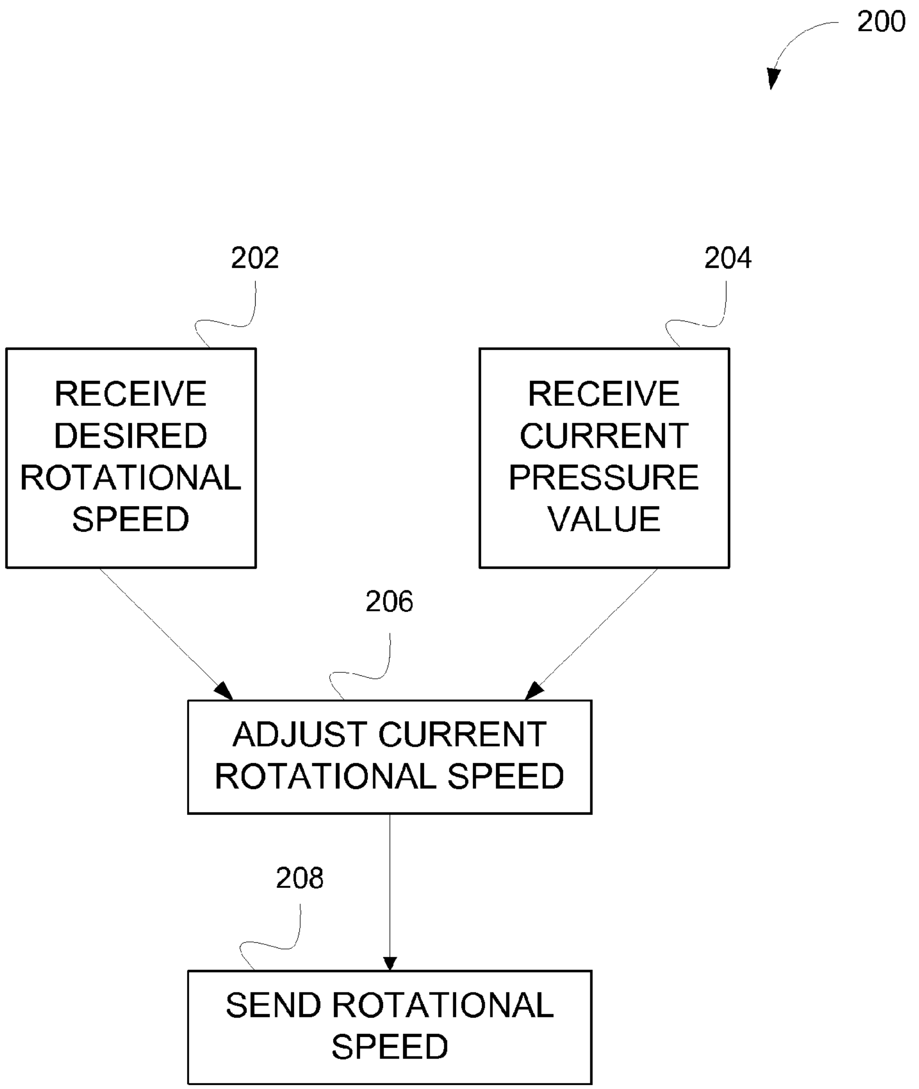
FIG. 2 is a flow diagram of a method for providing sexual stimulation, in accordance with an embodiment of the invention.

FIG. 2 is a flow diagram of a method for providing sexual stimulation, in accordance with an embodiment of the invention. In some embodiments, method 200 is performed by a hardware implementation of a system for providing sexual stimulation. Method 200 includes receiving a desired rotational speed 202; receiving a current pressure value 204; adjusting the current rotational speed 206; and sending a rotational speed 208.

At operation 202, the receiving a desired rotational speed may include receiving the desired rotational speed via a user interface, a remote control, or a data packet. In some embodiments, the system for providing sexual stimulation receives the desired rotational speed 202 from a rotary dial or other similar physical switch on the unit. In different embodiments, the system for providing sexual stimulation receives the desired rotational speed 202 from a remote control embodied in a different physical device connected by wire. In other embodiments, the system for providing sexual stimulation receives the desired rotational speed 202 from a data packet. For example, the system for providing sexual stimulation may include a wireless networking connection, such that a user at a remote computer can select the desired rotational speed.

At operation 204, the receiving a current pressure value may include receiving the current pressure value via a pressure sensor. In some embodiments, the system for providing sexual stimulation includes a pressure sensor that measures how firmly the device is held against a part of the body 106. The resulting pressure value enables the system to maintain a constant rotational speed even when significant force is being used to hold the device against the body, retarding the rotation.

At operation 206, the adjusting the current rotational speed may include adjusting the rotational speed for various received current pressure values 204. In some embodiments, the device attempts to maintain the rotational speed received at 202 irrespective of the current pressure value received at 204. For example, if the system senses more pressure being applied, the friction from which would slow the rotation, at operation 206 the system compensates for the added pressure by adjusting the rotational speed to keep it constant.

At operation 208, the sending a rotational speed may include sending a signal representing the speed at which the device should make rotations. In some embodiments, the device includes a motor, and the rotational speed of the motor is controlled by sending a rotational speed at 208, taking into account the rotational speed received at 202, compensating for any current pressure value received at 204, and adjusting the current rotational speed 206 accordingly.

Figure 3:
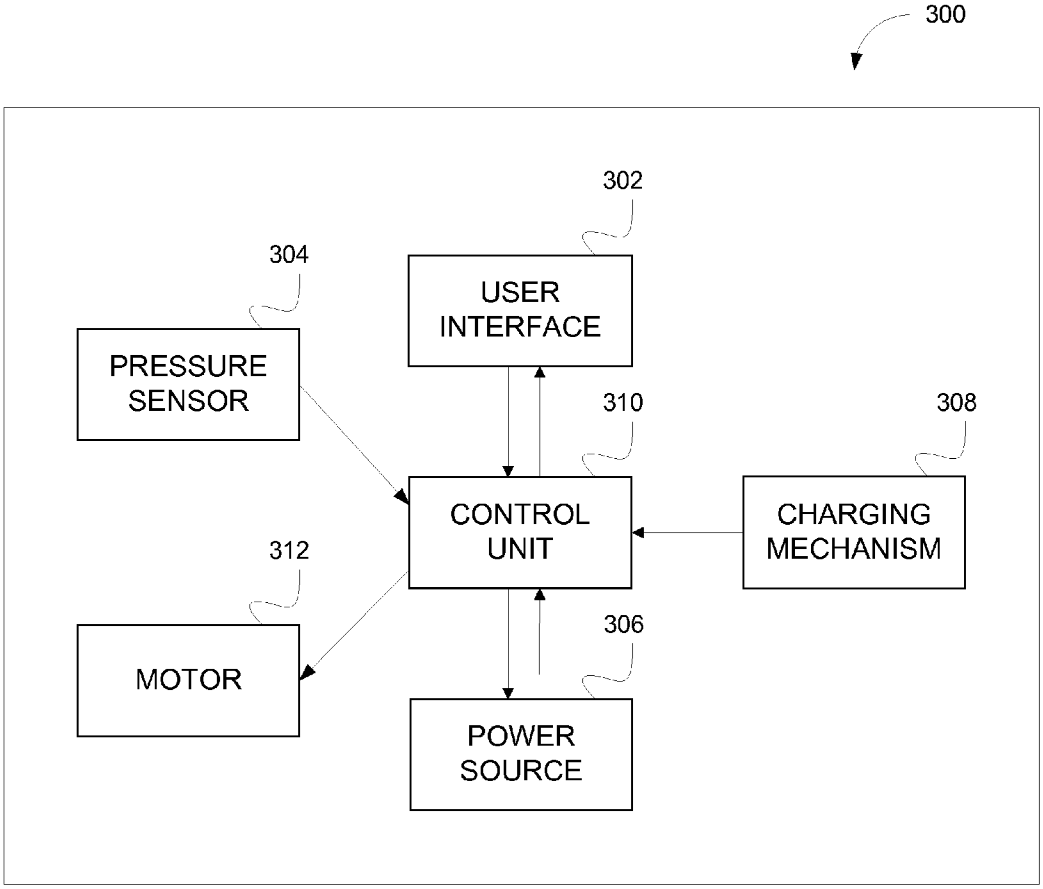
FIG. 3 is a block diagram of a system for providing sexual stimulation, in accordance with an embodiment of the invention.
Figure 4:
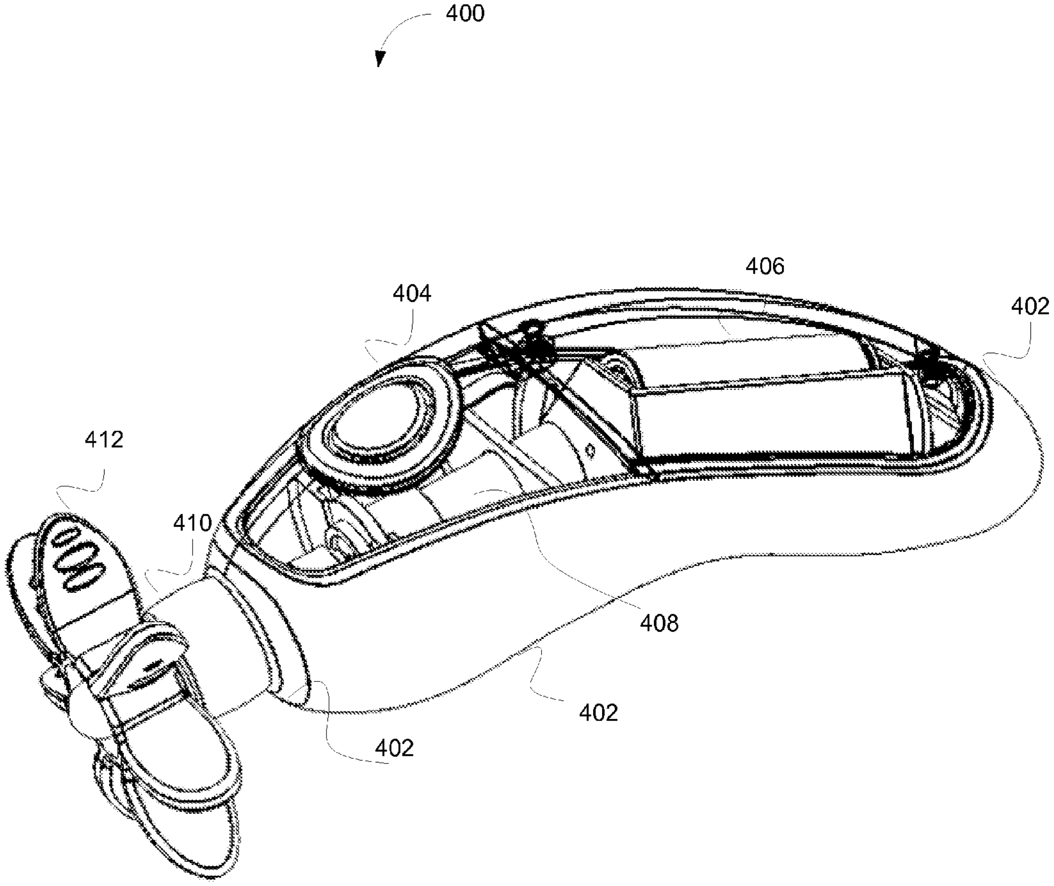
FIG. 4 is a partial perspective cross-sectional view of a system for providing sexual stimulation, in accordance with an embodiment of the invention.
Figure 5:
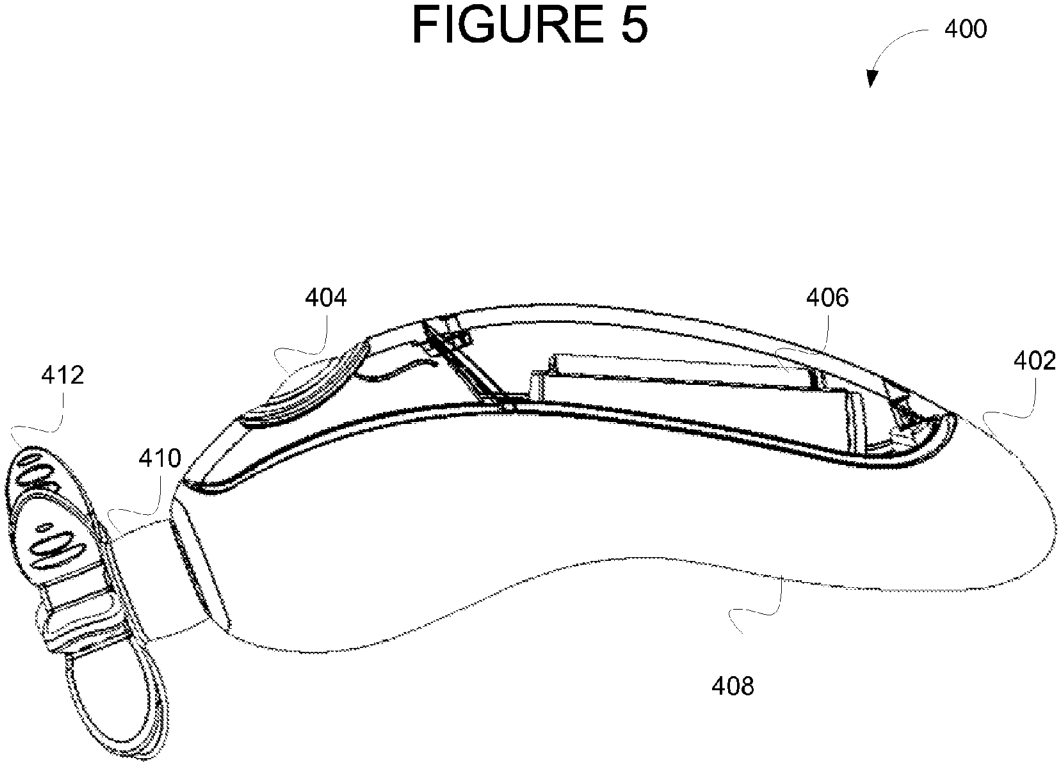
FIG. 5 is a partial side cross-sectional view of a system for providing sexual stimulation, in accordance with an embodiment of the invention.
Figure 6:
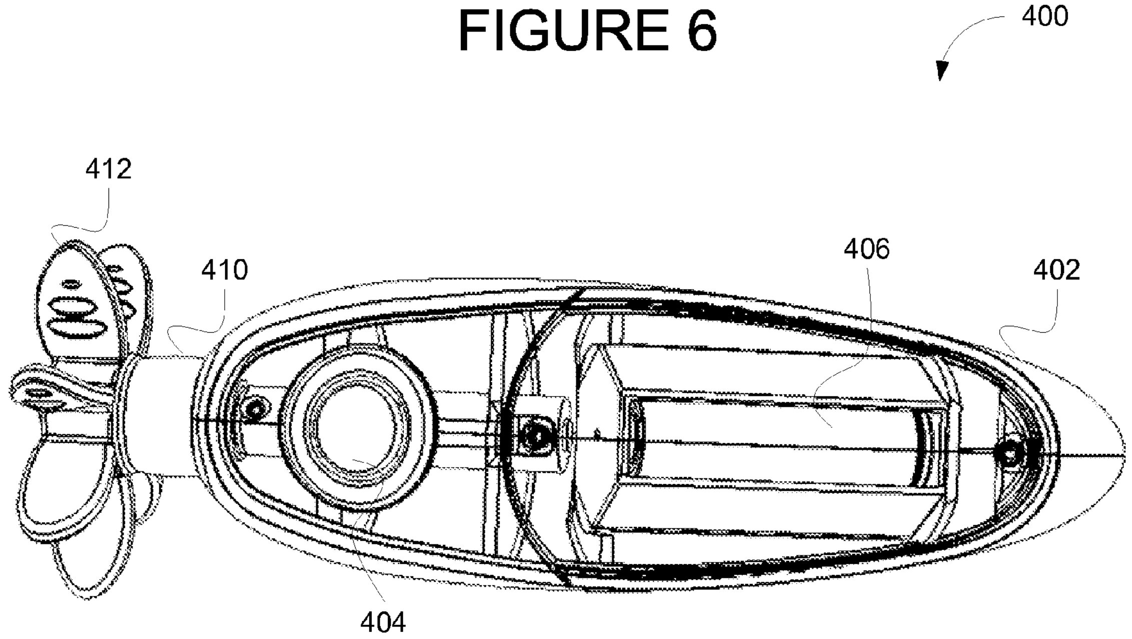
FIG. 6 is a partial top cross-sectional view of a system for providing sexual stimulation, in accordance with an embodiment of the invention.
Figure 7:
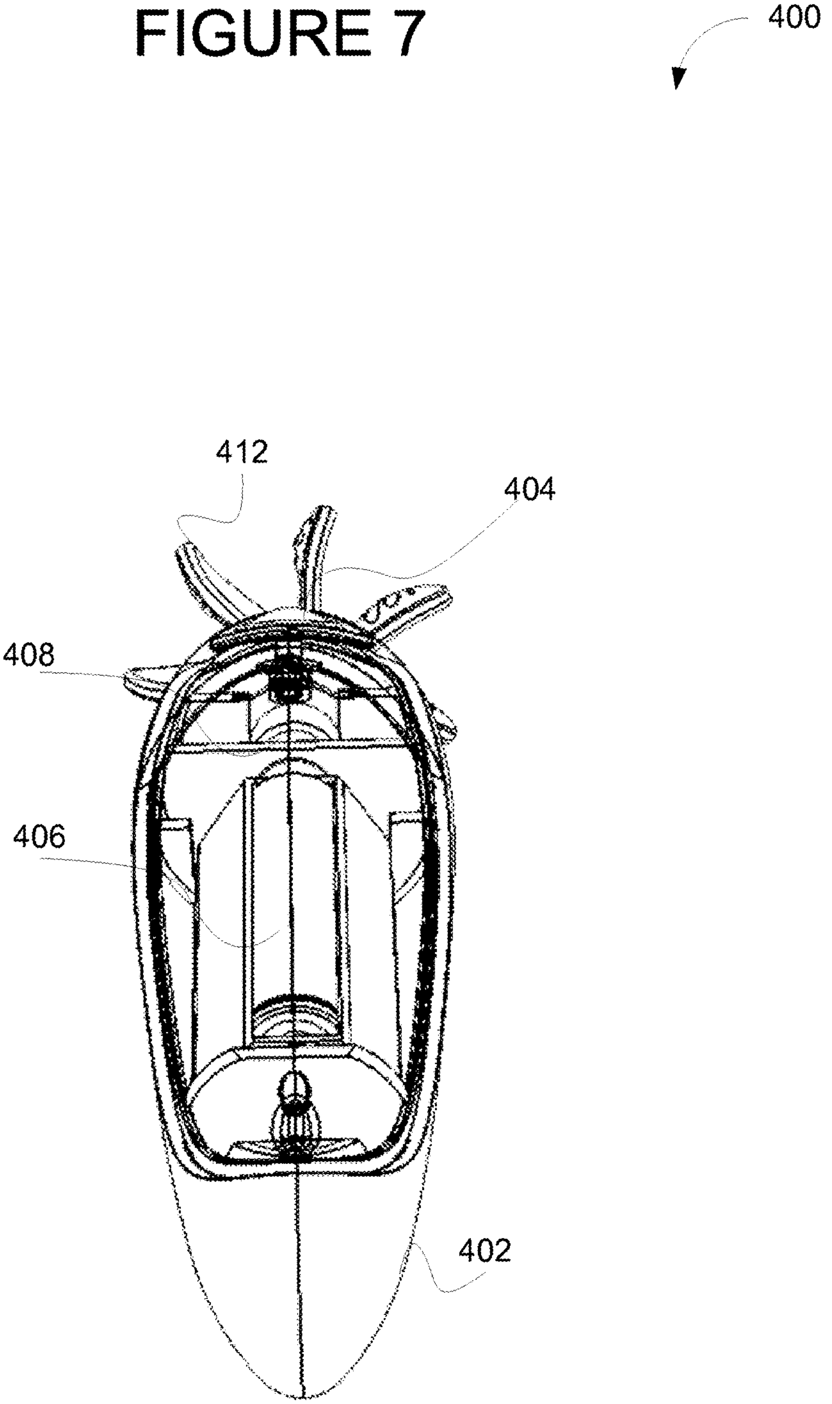
FIG. 7 is a partial top cross-sectional view of a system for providing sexual stimulation, in accordance with an embodiment of the invention.
Figure 8:
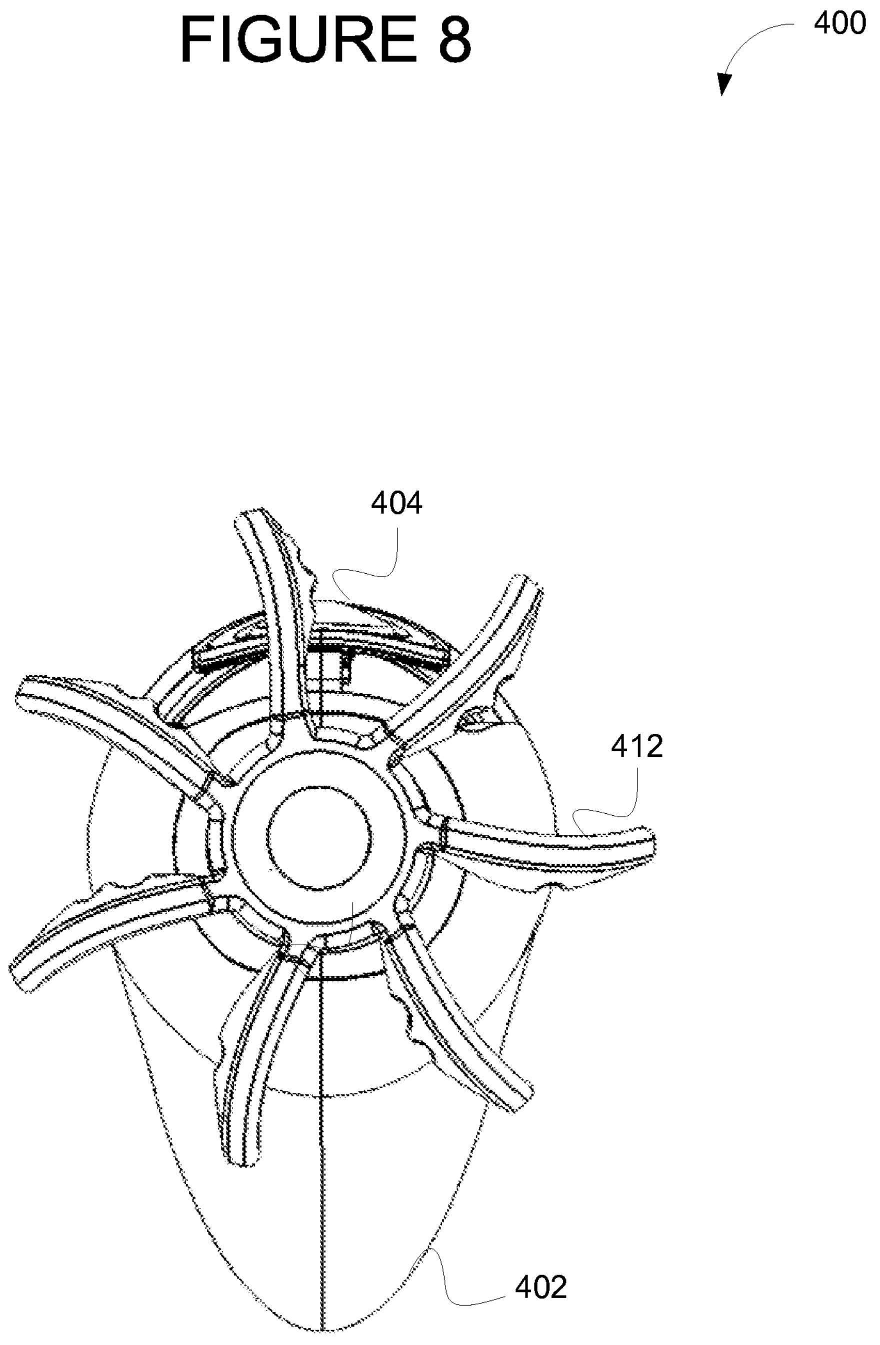
FIG. 8 is a front view of a system for providing sexual stimulation, in accordance with an embodiment of the invention.
Figure 9:
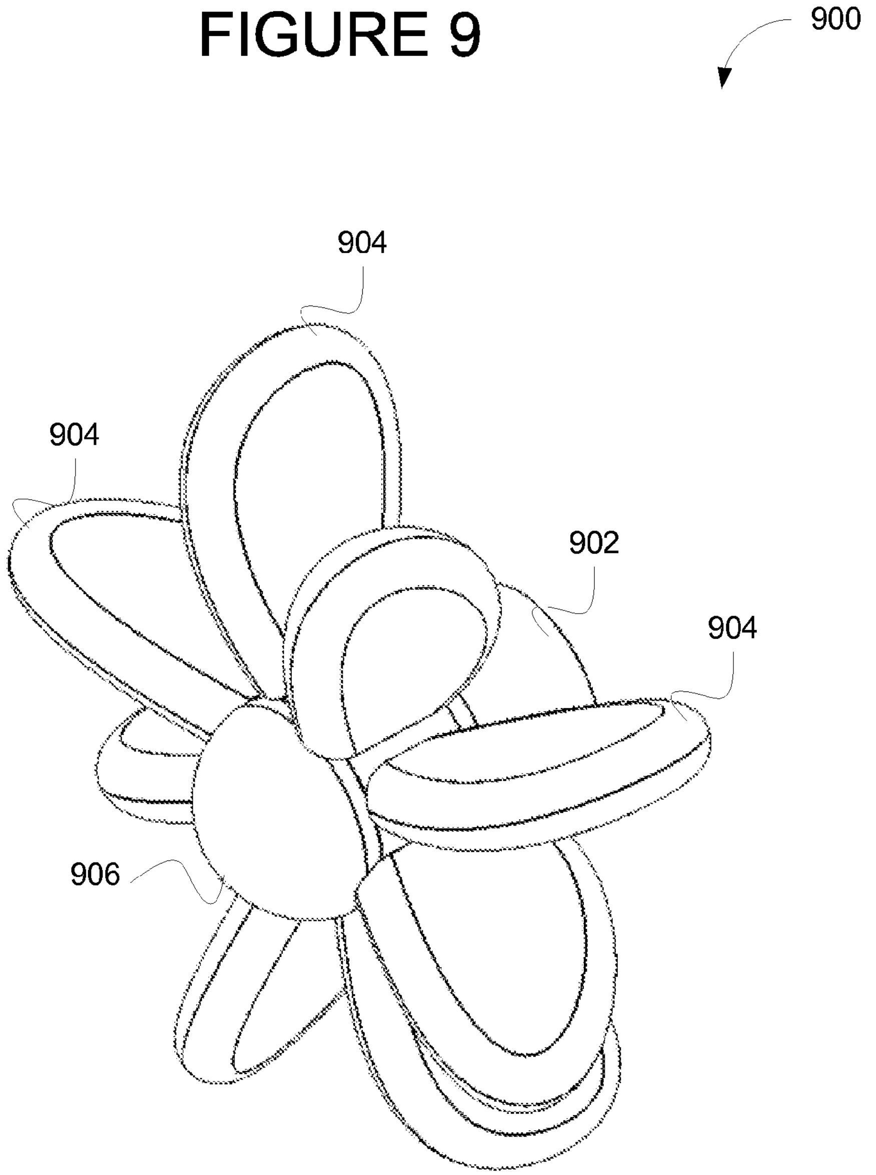
FIG. 9 is a perspective view of an attachment for a system for providing sexual stimulation, in accordance with an embodiment of the invention.
Figure 10:
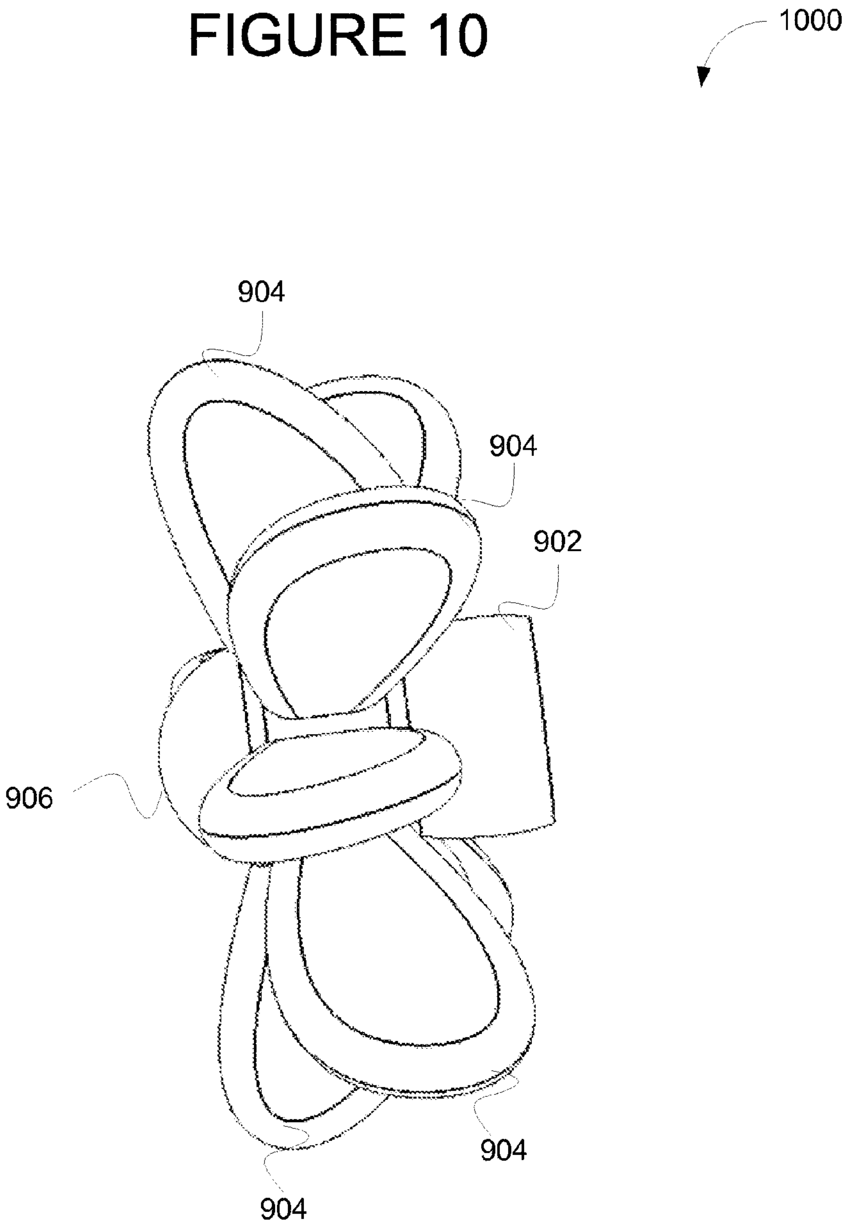
FIG. 10 is a side view of an attachment for a system for providing sexual stimulation, in accordance with an embodiment of the invention.
Figure 11:
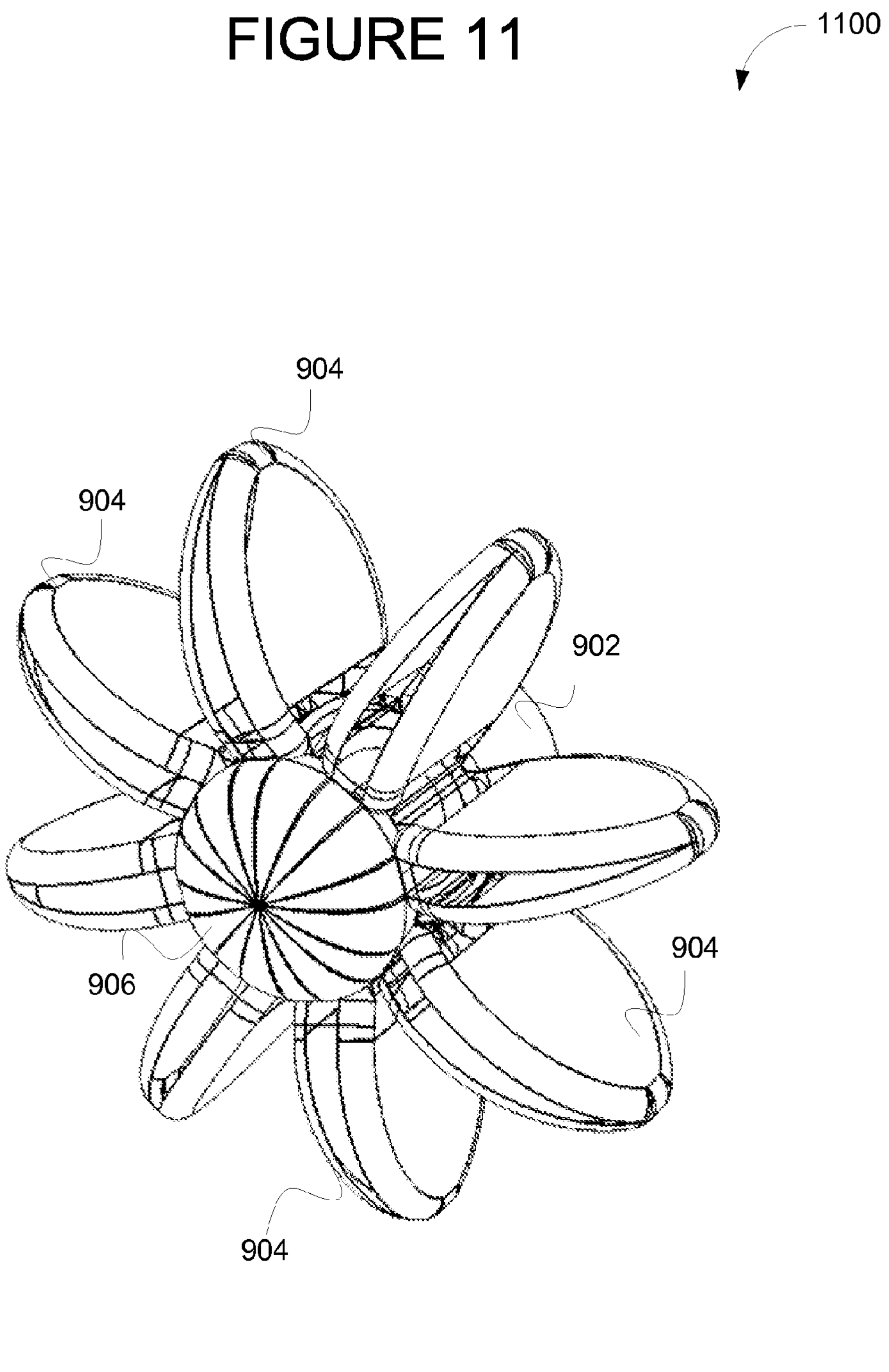
FIG. 11 is a perspective view of an attachment for a system for providing sexual stimulation, in accordance with an embodiment of the invention.
Figure 12:
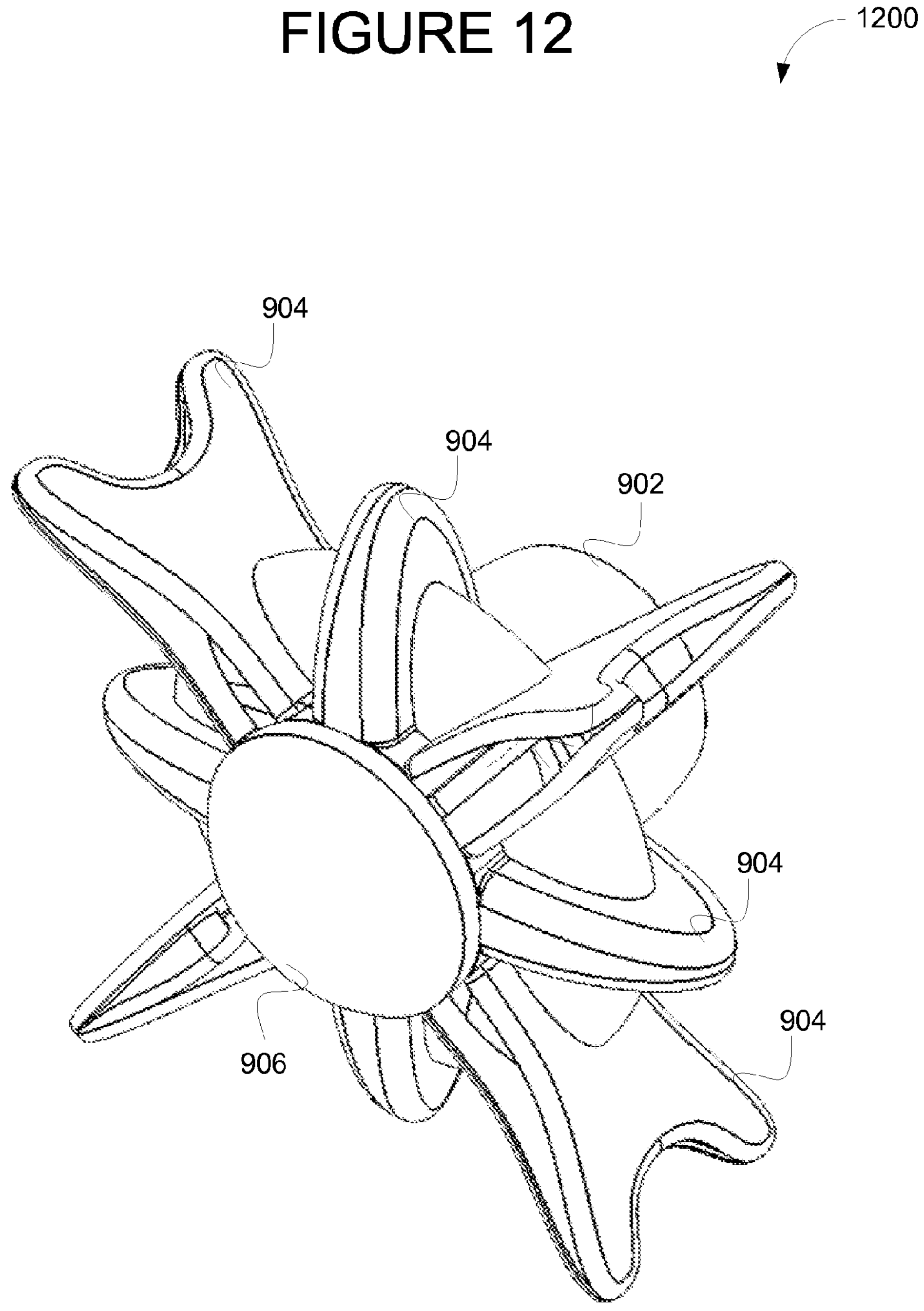
FIG. 12 is a perspective view of an attachment for a system for providing sexual stimulation, in accordance with an embodiment of the invention.
Figure 13:
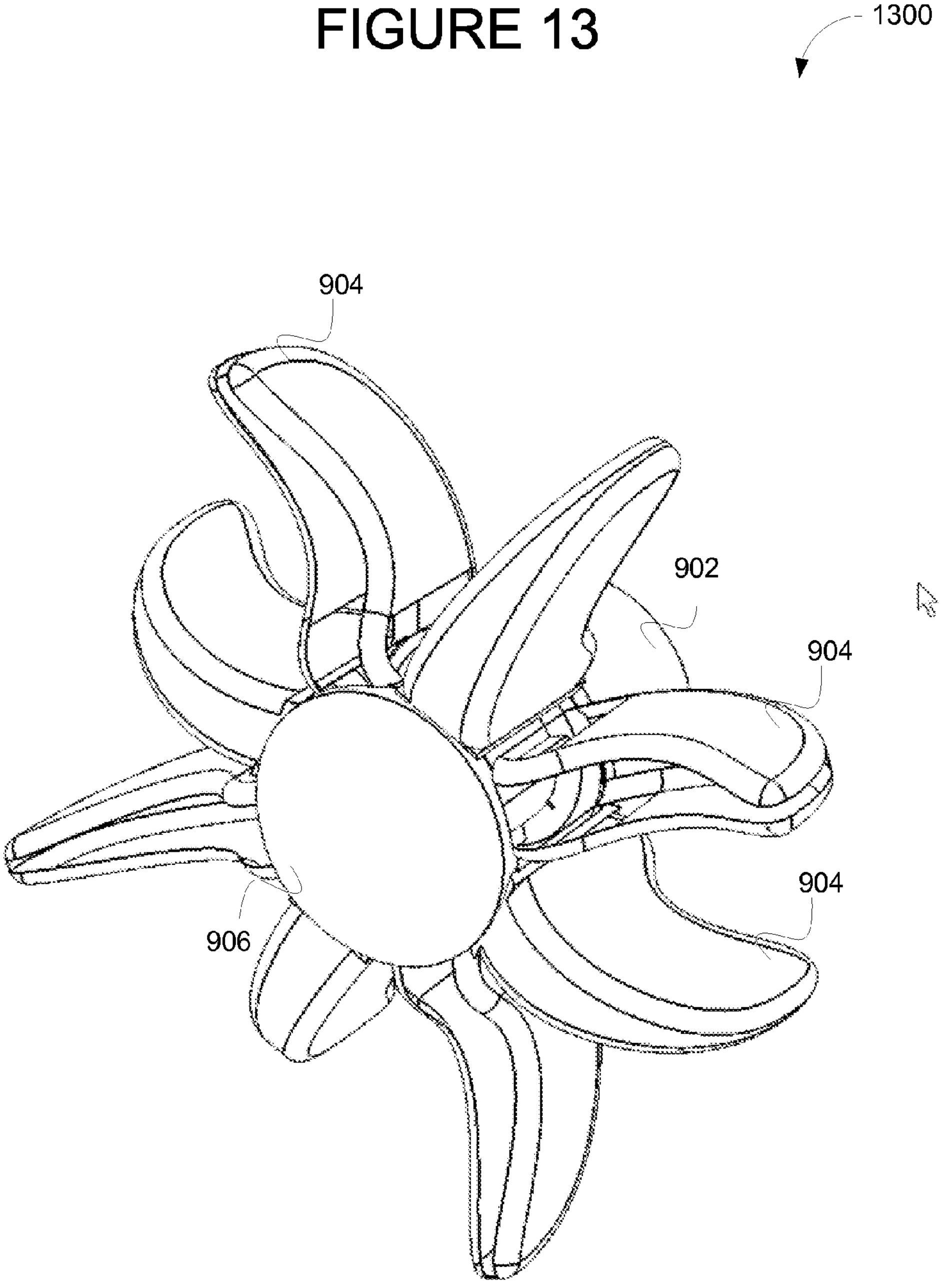
FIG. 13 is a perspective view of an attachment for a system for providing sexual stimulation, in accordance with an embodiment of the invention.

FIG. 3 is a block diagram of a system for providing sexual stimulation, in accordance with an embodiment of the invention. In one embodiment, a system for providing sexual stimulation includes a user interface 302, a pressure sensor 304, a power source 306, a charging mechanism 308, a control unit 310, and a motor 312. The user interface 302 enables the device to be turned on and off, and a rotational speed value to be selected. In some embodiments, the user interface 302 is a part of the device itself. In other embodiments, the user interface 302 is remote. In a certain embodiment, the user interface 302 is contained in a separate device, which is joined to this system by a wire. In another certain embodiment, the user interface 302 is contained in a separate device, which is joined to this system by a wireless connection. In some embodiments, the user interface 302 has lighting features. In other embodiments, the user interface 302 provides still or moving camera functionality. In some embodiments, the user interface 302 includes controls for other motions, which may include gyration, vibration, protrusion/retraction, displacement, and/or similar motions. In some embodiments, the user interface 302 is configured to enable the speed to be varied in a binary fashion, or in adjustable increments. In other embodiments, the user interface 302 can accept various audible commands at varying intensities. In further embodiments, the user interface 302 can make audible sounds, such as computer-generated tones or music, or simulated and/or recorded human voices. In different embodiments, the user interface 302 includes a projector configured to project images on a surface (e.g., a ceiling). In other embodiments, the user interface 302 is configured to send and/or receive data via wireless and/or wired communication (e.g., to present images to a remote individual and/or to allow that remote individual to at least partially control various aspects of the device for providing sexual stimulation). In other embodiments, the user interface 302 can include controlling a desired amount of lubricant to be dispensed.

The pressure sensor 304 provides a current pressure value. In some embodiments, the current pressure value represents the pressure with which the device is being pressed against a body part.

The power source 306 provides power to the device. In some embodiments, the power source 306 may be one or more disposable battery cells. In other embodiments, the power source 306 may be one or more rechargeable battery cells. In other embodiments, the power source 306 may be a direct connection to household electric power. In other embodiments, the power source 306 may be a direct connection to any source of electric power, including alternating or direct current, with any range of input voltage from 0 to 500 VDC (e.g. 9-220 VDC).

The charging mechanism 308 provides a means of providing power to the device. In some embodiments, the charging mechanism 308 is a direct electrical connection. In other embodiments, the charging mechanism 308 is a touch-free magnetic connection. In other embodiments, the charging mechanism 308 is a solar charge. In other embodiments, the charging mechanism 308 is one or more of the above charging mechanisms.

The control unit 310 receives input from the user interface 302 and the pressure sensor 304 to maintain a desired rotational speed. In some embodiments, the control unit 310 is powered by the power source 306. In other embodiments, the control unit 310 receives power directly from the charging mechanism 308. In certain embodiments, the control unit 310 diverts power from the charging mechanism 308 to the power source 306 to recharge the power source 306. In some embodiments, the control unit 310 controls output to the user interface 302. For example, the output to the user interface 302 could be display data, camera controls, networking packet data, an indication of remaining battery charge, an indication of the current speed and/or pressure, and/or other types of output. The control unit 310 may also include controls for lighting features of the device, or audio programming such as computer-generated tones, music and/or voices. The control unit 310 may facilitate different motions of which the device is capable, including gyration, vibration, protrusion/retraction, displacement, and/or similar motions.

The motor 312 receives a desired rotational speed from the control unit 310. The motor 312 drives a shaft to which various attachments are couplable. In one embodiment, the motor 312 is configured to cause rotation from approximately 0 to 1000 rpm (e.g., 0-200 rpm). In some embodiments, the motor speed is provided by the user interface at 302. In other embodiments, the motor 312 is capable of facilitating various motions, including gyration, vibration, protrusion/retraction, displacement, and/or similar motions. In a certain embodiment, the motor 312 has a cutoff feature where if too much pressure is applied that retards the motion of the motor, the motor stops operating before the motor experiences a mechanical fault.

FIGS. 4-8 are various views of a system for providing sexual stimulation, in accordance with an embodiment of the invention. In one embodiment, system 400 includes a housing 402, a user interface 404, a power supply 406, a motor 408, a housed shaft 410, and an attachment 412. When the user interface 404 is operated, the motor 408 spins the attachment 412 via the housed shaft 410, and the device 400 is applied to a part of the body providing sexual stimulation. For example, the applied to a part of the body providing sexual stimulation may include the attachment 412 pressed against the clitoris providing a simulation of cunnilingus.

In certain embodiments, the housing 402 is ergonomically designed to provide a comfortable grip when the device 400 is held by either the person being stimulated or by a partner. In certain further embodiments, the housing 402 is elongated and cylindrical. In certain other embodiments, the housing 402 is differently shaped, such as with a bend (e.g., an approximately 20 degree bend) to further improve ergonomics. In some embodiments, the housing 402 is adjustable in length and/or bend. In some embodiments, the housing 402 includes one or more posts to support the device 400 against a surface. In other embodiments, the housing 402 includes a strap so that the device 400 does not have to be gripped but is held in place by the strap, enabling easier use of the device 400 and/or use of the device 400 by those who are unable to grip it due to physical disability or arthritis. In another embodiment, the housing 402 is constructed of a sound-absorbing material to mask the noise of the motor 408 for less aural distraction and greater enjoyment.

In other embodiments, the housing 402 includes a removable cover to provide access to the compartment in which batteries are contained for a power source. In certain embodiments, the housing 402 is constructed of a squeezable rubber to minimize vibration and fatigue from holding the device 400. In other embodiments, the housing 402 is ornately designed with colors, jewels or other designs for a pleasing visual appearance. In some embodiments, the housing 402 is transparent. In other embodiments, the housing 402 contains lighting features, either for design effect or to cast illumination. In other embodiments, the housing 402 encompasses a reservoir in which lubricant can be stored and dispensed, and the housing 402 has a port for adding lubricant to the reservoir. In some embodiments, the housing 402 has a port for a recharging mechanism. In certain further embodiments, the port for the charging mechanism is hidden inside the housing 402, the housing 402 maintaining an airtight seal when there is no charging mechanism connected, but opening slightly when a charging plug is pushed into the housing 402. In certain further embodiments, the airtight seal of the rubber of the housing 402 is a septum.

In some embodiments, the user interface 404 is a speed control only, at which the lowest setting is off. In other embodiments, the user interface 404 has separate power and speed controls. In other embodiments, the user interface 404 includes controls to dispense lubricant. In other embodiments, the user interface 404 includes controls to change the motion of the device, including gyration, vibration, protrusion/retraction, displacement, and/or similar motions. In other embodiments, the user interface 404 enables the user to select whether the device 400 should maintain a constant rotational speed, or allow pressure to slow the device 400. In other embodiments, the user interface 404 is a touch screen allowing access to all functions of the device 400. In other embodiments, the user interface 404 displays information, such as the rotational speed, power source, or remaining charge of the battery. In some embodiments, the user interface 404 is configured to enable the speed to be varied in a binary fashion, or in adjustable increments. In other embodiments, the user interface 404 can accept various audible commands at varying intensities.

In some embodiments, the user interface 404 is a part of the device 400 itself. In other embodiments, the user interface 404 is remote. In a certain embodiment, the user interface 402 is contained in a separate device, which communicates with system 400 by a wire. In another certain embodiment, the user interface 404 is contained in a separate device, which communicates with system 400 by a wireless connection. In some embodiments, the user interface 404 has lighting features. In other embodiments, the user interface 404 provides still or moving camera functionality. In further embodiments, the user interface 404 can make audible sounds, such as computer-generated tones or music, or simulated and/or recorded human voices. In different embodiments, the user interface 404 includes a projector configured to project images on a surface (e.g., a ceiling). In other embodiments, the user interface 404 is configured to send and/or receive data via wireless and/or wired communication (e.g., to present images to a remote individual and/or to allow that remote individual to at least partially control various aspects of the device 400 for providing sexual stimulation). In other embodiments, the user interface 404 has a timer.

In some embodiments, the power supply 406 provides power to the device. In some embodiments, the power supply 406 may be one or more disposable battery cells. In other embodiments, the power supply 406 may be one or more rechargeable battery cells. In other embodiments, the power supply 406 may be a direct connection to household electric power. In other embodiments, the power supply 406 may be a direct connection to any source of electric power, including alternating or direct current, with any range of input voltage from 0 to 500 VDC (e.g., 9-220 VDC).

In some embodiments, the motor 408 drives a shaft to which removable hub assemblies are couplable. In some embodiments, the motor 408 is configured to cause rotation from approximately 0 to 1000 rpm (e.g., 0-200 rpm). In other embodiments, the motor 408 can provide a constant rotational speed irrespective of the pressure with which the device is held against a body part. In other embodiments, the motor 408 is capable of facilitating various motions, including gyration, vibration, protrusion/retraction, displacement, and/or similar motions. In a certain embodiment, the motor 408 has a cutoff feature where if too much pressure is applied that retards the motion of the motor 408, the motor 408 stops operating before the motor experiences a mechanical fault.

In some embodiments, the housed shaft 410 is directly driven by the motor 408 and is couplable to attachments 412. In other embodiments, the housed shaft 410 is driven the motor 408 by an angled gearing, the gearing provided to either facilitate a bend in the device, or to permit different rotational speeds of the motor 408 and housed shaft 410. In some embodiments, the housed shaft 410 is partially covered by the housing 402, and partially exposed when the attachment 412 is removed. In some embodiments, the housed shaft 410 is configured to removably receive one or more attachments. In some embodiments, the housed shaft 410 is configured to being substantially permanently coupled to one or more attachments 412. In some embodiments, the housed shaft 410 is articulatable. In other embodiments, the housed shaft 410 is configured to rotate obliquely. In other embodiments, the housed shaft 410 moves, shifts, and/or rotates under pressure to provide "give". In other embodiments, the housed shaft 410 may also house a pressure sensor.

In some embodiments, the housed shaft 410 houses a removable hub assembly. A removable hub assembly may include a hexagonal spindle, which may include two surface projections to resist attachment slippage. A hexagonal spindle may range from 0.25" to 24" in length (e.g., 1.25" in length). A hexagonal spindle may range from 0.1" to 3" in diameter (e.g., 0.25" in diameter). In other embodiments, the removable hub assembly is non-hexagonal (e.g., cylindrical, triangular, cubical, or other uniform or non-uniform shape) having length and diameter ranges articulated for the hexagonal spindle. In some embodiments, the removable hub assembly is a different uniform and/or non-uniform diameter and/or length. In some embodiments, a removable hub assembly is configured to being substantially permanently coupled to one or more attachments. In some embodiments, a removable hub assembly is magnetic. In some embodiments, a removable hub assembly couples via a ball and socket mechanism. In some embodiments, a removable hub assembly includes one or more surface projections, which may be differently positioned and/or differently shaped (e.g., no surface projections).

In some embodiments, the housed shaft 410 houses a fixed hub assembly. A fixed hub assembly may include a hexagonal spindle, which may include two surface projections to resist attachment slippage. A hexagonal spindle may range from 0.25" to 24" in length (e.g., 1.25" in length). A hexagonal spindle may range from 0.1" to 3" in diameter (e.g., 0.25" in diameter). In other embodiments, the fixed hub assembly is non-hexagonal (e.g., cylindrical, triangular, cubical, or other uniform or non-uniform shape) having length and diameter ranges articulated for the hexagonal spindle. In some embodiments, the fixed hub assembly is a different uniform and/or non-uniform diameter and/or length. In some embodiments, a fixed hub assembly is configured to being substantially permanently coupled to one or more attachments. In some embodiments, a fixed hub assembly is magnetic. In some embodiments, a fixed hub assembly couples via a ball and socket mechanism. In some embodiments, a fixed hub assembly includes one or more surface projections, which may be differently positioned and/or differently shaped (e.g., no surface projections).

In some embodiments, the attachment 412 is spun by the motor 408 via the housed shaft 410 with which the attachment 412 is couplable. In some embodiments, an attachment 412 includes a base having one or more paddles disposed thereon, wherein the one or more paddles are configured to contact a body part (e.g., a sexual body part) upon revolution of the attachment 412. In one embodiment, the attachment 412 is configured to removably circumscribe a removable or fixed hub assembly inside the housed shaft 410. In some embodiments, the attachment 412 includes one or more indentations to receive one or more surface projections of a removable or fixed hub assembly inside the housed shaft 410. In some embodiments, a plurality of attachments 412 are provided, each having a base with different placements, numbers, lengths, shapes, and/or sizes of paddles disposed thereon. In some embodiments, the attachment 412 is constructed of a porous, "weeping" material through which lubricant is dispensed over a period of time.

In some embodiments, variations of a number of paddles results in variation of contacts/unit of time (e.g., 4 paddles at 100 rpm results in 400 contacts per minute and 8 paddles at 100 rpm results in 800 contacts per minute). In some embodiments, variations of a length of paddles results in variations of force/contact (e.g., a short paddle results in more force per contact than a long paddle). In some embodiments, a number of paddles of an attachment 412 may range from approximately 1 to 1000 (e.g., around 4 to 8). In some embodiments, a length of paddles of an attachment 412 may range from approximately 0.01" to 24" (e.g., around 0.25" to 1"). In some embodiments, a width of paddles of an attachment 412 may range from approximately 0.01" to 5" (e.g., 0.25" to 0.375"). In some embodiments, a placement of paddles of an attachment 412 may be uniform, alternative, and/or random (e.g., each paddle being aligned, successive paddles being oppositely disposed along sides of an attachment 412, successive paddles being randomly disposed along a width of an attachment 412). In some embodiments, a rotation of paddles of an attachment 412 may be uniform, alternative, and/or random (e.g., successive paddles being rotated slightly relative to one another). In some embodiments, a paddle may be rounded, flat, or some other uniform and/or non-uniform shape. In some embodiments, a paddle may include a plurality of strands, strings and/or hair or hair-like structures. In some embodiments, a paddle may be rotatable, anglable, vibratable, gyratable, and/or configurable to protrude and/or retract relative to an attachment 412 base. In some embodiments, a paddle moves, shifts, and/or rotates under pressure to provide "give". In some embodiments, a paddle may include one or more internal channels to deliver lubricant. In some embodiments, a paddle may include a lighting feature to achieve either a design effect, illumination, or for any other purpose. In some embodiments, a paddle may be movable, removable, and/or replaceable relative to an attachment 412 base. In some embodiments, a plurality of different removable attachments 412 may be provided each having varying numbers, sizes and/or placements of paddles. In some embodiments, an attachment 412 is configured to substantially permanently couple to a removable hub assembly contained in the housing shaft 410. In some embodiments, an attachment 412 is composed of silicone or other similar material. In some embodiments, an attachment 412 has a varied texture including ridges, nubs, or other protrusions or cavities. In some embodiments, an attachment 412 has a cavity into which another device, such as a vibrating dildo can be inserted, providing sexual stimulation such as penetration into a human body. In some embodiments, an attachment 412 has no paddles and no cavity and is itself a dildo, which may or may not vibrate, which provides sexual stimulation such as penetration into a human body.

FIGS. 9-13 are various views of attachments for a system for providing sexual stimulation, in accordance with embodiments of the invention. In one embodiment, an attachment 900 includes a base 902 and one or more paddles 904. In some embodiments, an attachment 900 may further include a rubber cover at 906. In other embodiments, an attachment 900 may have a solid center at 906.

In some embodiments, an attachment 900 has a base 902 which circumscribes a cavity by which a spindle or other removable or fixed hub assembly inside the housed shaft 410 is couplable.

In some embodiments, an attachment 900 has one or more paddles 904 disposed thereon, wherein the one or more paddles 904 are configured to contact a body part (e.g., a sexual body part) upon revolution of the attachment 900. In one embodiment, the attachment 900 is configured to removably circumscribe a removable or fixed hub assembly inside the housed shaft 410. In some embodiments, the attachment 900 includes one or more indentations to receive one or more surface projections of a removable or fixed hub assembly inside the housed shaft 410. In some embodiments, a plurality of attachments 900 are provided, each having a base 902 with different placements, numbers, lengths, shapes, and/or sizes of paddles 904 disposed thereon. In some embodiments, the attachment 900 is constructed of a porous, "weeping" material through which lubricant is dispensed over a period of time.

In some embodiments, variations of a number of paddles 904 results in variation of contacts/unit of time (e.g., 4 paddles 904 at 100 rpm results in 400 contacts per minute and 8 paddles 904 at 100 rpm results in 800 contacts per minute). In some embodiments, variations of a length of paddles 904 as in FIG. 12 results in variations of force/contact (e.g., a short paddle 904 results in more force per contact than a long paddle 904). In some embodiments, a number of paddles 904 of an attachment 900 may range from approximately 1 to 1000 (e.g., around 4 to 8). In some embodiments, a length of paddles 904 of an attachment 900 may range from approximately 0.01" to 24" (e.g., around 0.25" to 1"). In some embodiments, a width of paddles 904 of an attachment 900 may range from approximately 0.01" to 5" (e.g., 0.25" to 0.375"). In some embodiments, a placement of paddles 904 of an attachment 900 may be uniform, alternative, and/or random (e.g., each paddle 904 being aligned as in FIG. 11, successive paddles 904 being oppositely disposed along sides of an attachment 900 as in FIG. 13, successive paddles 904 being randomly disposed along a width of an attachment 900). In some embodiments, a rotation of paddles 904 of an attachment 900 may be uniform, alternative, and/or random (e.g., successive paddles 904 being rotated slightly relative to one another). In some embodiments, a paddle 904 may be rounded, flat, or some other uniform and/or non-uniform shape. In some embodiments, a paddle 904 may include a plurality of strands, strings and/or hair or hair-like structures. In some embodiments, a paddle 904 may be rotatable, anglable, vibratable, gyratable, and/or configurable to protrude and/or retract relative to an attachment 900 base 902. In some embodiments, a paddle 904 moves, shifts, and/or rotates under pressure to provide "give". In some embodiments, a paddle 904 may include one or more internal channels to deliver lubricant. In some embodiments, a paddle 904 may include a lighting feature to achieve either a design effect, illumination, or for any other purpose. In some embodiments, a paddle 904 may be movable, removable, and/or replaceable relative to an attachment 900 base 902. In some embodiments, a plurality of different removable attachments 900 may be provided each having varying numbers, sizes and/or placements of paddles 904. In some embodiments, an attachment 900 is configured to substantially permanently couple to a removable hub assembly contained in the housing shaft 410. In some embodiments, an attachment 900 is composed of silicone or other similar material. In some embodiments, an attachment 900 has a varied texture including ridges, nubs, or other protrusions or cavities. In some embodiments, an attachment 900 has a cavity into which another device, such as a vibrating dildo can be inserted, providing sexual stimulation such as penetration into a human body. In some embodiments, an attachment 900 has no paddles and no cavity and is itself a dildo, which may or may not vibrate, which provides sexual stimulation such as penetration into a human body.

While preferred and alternative embodiments of the invention have been 470 illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A device for providing sexual stimulation, comprising:
- a housing;
- a shaft, the shaft at least partially extending from the housing, the shaft removably receiving at least one attachment, the at least one attachment including at least one or more paddles, wherein the one or more paddles of an attachment received by the shaft are exterior to the housing;
- a user interface, including at least one control disposed on the housing, the at least one control configured to receive a rotational speed for the shaft;
- a motor contained by the housing, the motor rotatably coupled with the shaft;
- one or more pressure sensors coupled with at least one of the shaft or the motor, the one or more pressure sensors configured to sense pressure transmitted via the shaft, the pressure resulting from one or more paddles physically contacting an object external to the device;
- a control unit configured to control the motor to rotate the shaft at least partially based on a rotational speed received via the user interface, the control unit further configured to control the motor at least partially based on a pressure sensed by the one or more pressure sensors; and
- a power source, the power source configured to provide power to at least the motor.

2. The device of claim 1, wherein the attachments comprise:
- a plurality of paddles around a cylindrical hub, the paddles having varying uniform or non-uniform shapes, textures, and malleability.

3. The device of claim 2, wherein the cylindrical hub has a cover which can be removed, revealing a reservoir into which a vibrating device can be inserted.

4. The device of claim 1, wherein the housing includes at least a strap.

5. The device of claim 1, wherein the power source is a rechargeable battery.

6. The device of claim 1, further comprising:
- a charging port in the housing, the charging port in the housing forming an airtight seal of the housing when the charging port is in a closed state and allowing a connection with a corded power supply when the charging port is in an open state.

7. The device of claim 1, wherein the shaft, the shaft at least partially extending from the housing comprises:
- a shaft including at least a hexagonal spindle, wherein at least a portion of the hexagonal spindle extends through the housing and is accessible from the exterior of the housing, the hexagonal spindle configured to receive an attachment having a hexagonal socket.

8. The device of claim 1, wherein the shaft, the shaft at least partially extending from the housing comprises:
- a magnetic shaft at least partially extending from the housing, wherein an end of the shaft extending to the exterior of the housing is configured to magnetically couple with one or more magnetized attachments including at least one or more paddles.

9. The device of claim 1, wherein the control unit further comprises:
- the control unit configured to disengage the motor upon the one or more pressure sensors sensing a pressure above a threshold value, the threshold value established to prevent damage to the motor if too much pressure is sensed.

10. The device of claim 1, wherein the power source comprises:
- one or more disposable batteries, the one or more disposable batteries insertable in the housing via a compartment door disposed through the housing.

11. The device of claim 1, wherein the power source comprises:
- a direct connection to household electric power.

12. The device of claim 1, wherein the control unit comprises:
- a control unit operable to facilitate different motions of which the device is capable, including one or more of gyration, vibration, protrusion, retraction, or displacement.

13. The device of claim 1, wherein the housing comprises:
- a cylindrical housing.

14. The device of claim 1, wherein the housing comprises:
- a housing constructed of sound-absorbing material.

15. The device of claim 1, wherein the user interface comprises:
- a user interface wherein at least a portion of the user interface wirelessly controls operation of the device.

16. The device of claim 1, wherein the at least one attachment comprises:
- at least one attachment constructed of a porous material facilitating a lubricant passing through the at least one attachment.

17. The device of claim 1, wherein the at least one attachment comprises:
- at least one attachment including at least a plurality of paddles randomly disposed along a width of the at least one attachment.

18. The device of claim 1, further comprising:
- a camera; and
- a transmitter.

19. A system for providing sexual stimulation, comprising:
- a device including at least:
- a housing;
- a shaft, the shaft at least partially extending from the housing, the shaft removably receiving at least one attachment, the at least one attachment including at least one or more paddles, wherein the one or more paddles of an attachment received by the shaft are exterior to the housing;

a user interface, including at least one control disposed on the housing, the at least one control configured to receive a rotational speed for the shaft;

a motor, the motor contained by the housing, the motor rotatably coupled with the shaft;

one or more pressure sensors coupled with at least one of the shaft or the motor, the one or more pressure sensors configured to sense pressure transmitted via the shaft, the pressure resulting from one or more paddles physically contacting an object external to the device; and a power source, the power source configured to provide power to at least the motor; and circuitry maintaining a constant rotational speed of the motor, including at least circuitry sensing one or more pressure values via at least one of the one or more pressure sensors and circuitry altering the control of the motor at least partially based on a received rotational speed via the user interface and the sensed one or more pressure values.

20. A method, comprising:

providing a device for providing sexual stimulation, the device including at least:

a housing;

a shaft, the shaft at least partially extending from the housing, the shaft removably receiving at least one attachment, the at least one attachment including at least one or more paddles, wherein the one or more paddles of an attachment received by the shaft are exterior to the housing;

a user interface, including at least one control disposed on the housing, the at least one control configured to receive a rotational speed for the shaft;

a motor contained by the housing, the motor rotatably coupled with the shaft;

one or more pressure sensors coupled with at least one of the shaft or the motor, the one or more pressure sensors configured to sense pressure transmitted via the shaft, the pressure resulting from one or more paddles physically contacting an object external to the device;

a control unit configured to control the motor to rotate the shaft at least partially based on a rotational speed received via the user interface, the control unit further configured to control the motor at least partially based on a pressure sensed by the one or more pressure sensors; and a power source, the power source configured to provide power to at least the motor;

receiving, at the user interface of the device for providing sexual stimulation, a selection of a rotational speed;

controlling, via the control unit of the device for providing sexual stimulation, the motor of the device for providing sexual stimulation based at least partially on the received selection of a rotational speed;

determining, via the one or more pressure sensors of the device for providing sexual stimulation, one or more pressure values associated with pressure resulting from physical contact with an object external to the device; and maintaining, via the control unit of the device for providing sexual stimulation, a constant rotational speed based at least partially on the received selection of a rotational speed and on at least one of the determined one or more pressure values.

* * * * *